United States Patent [19]

Shindo et al.

[11] Patent Number: 4,604,418

[45] Date of Patent: Aug. 5, 1986

[54] PROCESS FOR ISOCYANURATING HEXAMETHYLENE-DIISOCYANATE USING A SODIUM OR POTASSIUM CARBOXYLATE CATALYST AND A PAINT COMPOSITION COMPRISING THE PRODUCT OF SAID PROCESS AND POLYOLS

[75] Inventors: Masanori Shindo, Fujisawa; Yusuke Aoki, Yokohama; Yosizumi Kataoka, Ota-ku; Susumu Enomoto, Yokohama; Minoru Nakamura, both of Yokohama, all of Japan

[73] Assignee: Nippon Polyurethane Industry Co., Ltd., Tokyo, Japan

[21] Appl. No.: 640,119

[22] Filed: Aug. 13, 1984

Related U.S. Application Data

[63] Continuation-in-part of Ser. No. 380,885, May 21, 1982, abandoned.

[30] Foreign Application Priority Data

Mar. 19, 1982 [JP] Japan ................................. 57-43864

[51] Int. Cl.$^4$ ............................................ C08L 75/04
[52] U.S. Cl. .................................... 524/296; 524/314; 524/377; 525/123; 528/48; 528/49; 528/51; 528/53
[58] Field of Search ....................... 528/48, 49, 51, 53; 524/296, 314, 377; 525/123

[56] References Cited

U.S. PATENT DOCUMENTS

| | | | |
|---|---|---|---|
| 2,978,449 | 4/1961 | France et al. | 544/193 |
| 3,284,413 | 11/1966 | Heiss et al. | 544/193 |
| 4,288,586 | 9/1981 | Bock et al. | 528/73 |

FOREIGN PATENT DOCUMENTS 920080 3/1963 United Kingdom .

OTHER PUBLICATIONS

Saunders et al, *Polyurethanes* Part I, Interscience, NY, 1962, pp. 86–88.
ASTM D 1638-74, pp. 146–147, 1974.
Saunders et al, *Polyurethanes,* Part I, Interscience, N.Y. 1963, pp. 94 and 95.

*Primary Examiner*—Maurice J. Welsh
*Attorney, Agent, or Firm*—Stevens, Davis, Miller & Mosher

[57] ABSTRACT

The invention relates to a process for isocyanurating hexamethylene-diisocyanate containing polyol adduct thereof using a novel catalyst and to a paint composition formed from of the product of the above mentioned process and polyol, and to the composition yielding a paint film showing an excellent light resistance and weather resistance, especially high yellowing resistance.

23 Claims, No Drawings

PROCESS FOR ISOCYANURATING HEXAMETHYLENE-DIISOCYANATE USING A SODIUM OR POTASSIUM CARBOXYLATE CATALYST AND A PAINT COMPOSITION COMPRISING THE PRODUCT OF SAID PROCESS AND POLYOLS

This application is a continuation-in-part of U.S. application Ser. No. 380,885, filed on May 21, 1982 and now abandoned.

This invention relates to a polyurethane paint composition and more to a novel urethane paint composition comprising polyols and isocyanurate rings containing polyisocyanates, and to a process for preparing an isocyanurate compound which comprises trimerising a reaction product of hexamethylene diisocyanate and a small amount of polyols; said polyisocyanurates helping to impart the polyurethane paint composition with superior weather resistance.

Polyurethane resin is well known in the art, and provides superior paint composition. The paint has been used to various fields of application by modifying the resin. For example, the resin, or paint composition thereof is widely used as paint for metals, plastics, glasses, wooden articles and the like.

However, urethane paints have weak points, such as, low heat, light and weather resistance, especially on its inferior non-yellowing property, and thus wide studies have been made to eliminate these weak points from the resin.

The invention also relates to improvement on weather resistance, especially non-yellowing property of urethane resin, using as isocyanate source isocyanurate compound of partially polyol modified hexamethylene diisocyanate, isocyanurated HDI. Although an excellent result would be expected from isocyanuration of aliphatic isocyanate, it has been considered a difficult problem in the technical field of the urethane industry.

Heretofore, aliphatic diisocyanates has been used in the form of polyol-adduct or biuret modified compounds. These compounds show superior light resistance and good heat resistance, but possess poor weather resistance and inferior non-yellowing properties.

Regarding the isocyanuration of organic compounds, wide studies have been carried out chiefly on aromatic isocyanates, but seldom on aliphatic isocyanates.

Regarding isocyanuration of aromatic compounds, Japanese Patent Gazett No. 5838/1965, and Japanese Laid Open Gazette Nos. 69497/1977 and 32490/1976, disclose that tertiary amines, tertiary phosphines, metal salts of acetyl acetone or metal salts of organic acids and the like are effective for isocyanuration of aromatic isocyanates.

In the field of aromatic isocyanates, although various improvements have been made and, several types of paints have been brought onto the market, they generally show an inferior non-yellowing property and thus this type of paint has not been used outdoors.

Since the urethane paint derived from aromatic isocyanate has such a defect, the development of a paint with superior heat and weather resistance, and especially superior non-yellowing properties has been sought.

Isocyanuration of aliphatic isocyanates has not been studied as much as aromatic diisocyanate compounds. The subsequent disclosure will be directed to isocyanuration of aliphatic isocyanates in reference to hexamethylene diisocyanate (refer to as HDI hereinafter) in the following.

Isocyanuration of HDI has been considered especially difficult among aliphatic diisocyanate compounds. Isocyanurated HDI shows very poor compatibility with HDI monomers and solvents to easily cause turbidity in a product of trimerization of HDI. Furthermore, a catalyst suitable for isocyanuration of aliphatic diisocyanates, especially of HDI, has not yet been discovered with known catalysts, it is liable to form highly polymerized products which cause turbidities in final products. For these reasons, isocyanurated products of HDI, have not yet been brought to practical use.

By conducting an intense study on isocyanuration of aliphatic isocyanates, especially on HDI, it has now been found that these known catalysts are effective for aromatic isocyanates, but they are ineffective for aliphatic ones, because they are too strong to cause a smooth reaction on aliphatic isocyanate components, i.e., they show one kind of selectivity on an isocyanate component to be reacted.

In other words, conventional catalysts are severly selective with respect to the reaction components; they show positive reactivity on aromatic isocyanates to cause normal trimerization, but they reveal negative reactivity on trimerization of aliphatic isocyanates to cause abnormal reaction. Thus, only some limited catalysts are effective for isocyanuration of aliphatic isocyanates, especially for HDI.

When these conventional catalysts are applied to isocyanuration of HDI they do not cause isocyanuration of HDI, but cause dimerization of HDI instead with trimerization of HDI. A dimer compound is unstable and simply causes dissociation by heating. Therefore, the isocyanurated compound containing dimer cannot merit the benefits of advantageous properties of isocyanurated rings of HDI on paint. Even in the use of a catalyst which forms a dimer in a relatively small amount, the catalyst exerts a strong catalytic action on HDI to bring about a local catalytic reaction to form insolubles in products.

The inventors have succeeded in developing isocyanuration of HDI, using partially polyoled HDI with a novel catalyst and found that a paint derived from the isocyanurated HDI shows very superior heat and weather resistance, and especially an excellent non-yellowing property. (Note: the term "polyoling" or "polyol modification" of HDI will be explained hereinafter).

Therefore, the present invention provides a process for preparing the trimer of HDI using partially polyoled HDI and a novel catalyst and a resin composition for urethane paint comprising of said trimer containing 10% to 60% by weight of isocyanurate rings and a polyol having a molecular weight higher than 600.

Namely, the present invention provides a process for preparing HDI trimer having isocyanurate rings which comprise trimerizing HDI containing partially polyol-modified ones in the presence of potassium or sodium salt of linear or branched aliphatic carbonic acid having the following formula:

$$C_nH_{2n+1}COOM$$

wherein M stands for potassium or sodium metal, and n for an integer of 2 to 10, preferably 3 to 9.

According to the invention, HDI is modified with polyol in an amount less than 15 mol% of total isocyanate radicals using diols or triols under conventional polyoling conditions for usual isocyanate compounds.

The obtained polyoled product will be used for isocyanuration as it is. Furthermore, in the use of partially polyol modified HDI, a local reaction never occurs and isocyanuration reaction can be advanced smoothly. The isocyanurated product obtained also shows superior compatibility with other components used or produced in the reaction, because the formation of highly polymerized compounds can be controlled as little as possible.

Furthermore, in the invention, the trimerization of HDI is controlled to an extent of 60% of total isocyanurate radicals entered into isocyanuration reaction. By this, the formation of highly polymerized products can be further controlled as little as possible.

When the reaction advances far, a highly polymerized polymer will be formed. It helps to improve heat and weather resistance of the product but is not desirable from the view of improvement of compatibility. For this reason, the reaction should be limited within 60% of the reaction range of the theoretical value of the invention.

The highly polymerized polymer often has a molecular weight of about 1.5 to about 3.0 folds of that of HDI trimer.

As mentioned in the above, in the present invention, HDI is modified with polyol in an amount less than 15 mol% of total isocyanate radicals modified with polyol and takes part in the isocyanuration reaction as it is. The isocyanuration reaction is conducted using the catalysts mentioned above with a promotor. The reaction is to be stopped at a reaction rate less than 60% as based on the theoretical reaction rate using strong acid; the promoter may be phenolic or alcoholic OH compounds.

By using HDI partially modified with polyol in an amount less than about 15 mol% of HDI, isocyanurating reaction is smoothly conducted, and the compatibility of the obtained product is highly improved.

Polyolization of HDI, namely, formation of partially polyol-modified HDI, is carried out by adding predetermined amounts of polyol to HDI and heating the reaction mixture at a temperature lower than 100° C., preferably between 70° and 100° C., for 2 hours. When reaction temperature is higher than 100° C., the reaction mixture will be colored or side reactions will occur.

Polyols used for polyol modification of HDI have a molecular weight less than 3,000 and has a functionalities of 2 to 3. They are illustrated as follows and may be used alone or in admixture.

As diols, there are mentioned as dihydric alcohols such as ethyleneglycol, diethylene-glycol, 1,3-butanediol (hereinafter referred to as 1,3BG), 1,4-butane-diol, propylene-glycol, dipropylene-glycol, neopentylglycol, 1,6-hexane-glycol (hereinafter referred to as 1,6BG); polyester-polyols, polyether-polyols and the like.

Among triols, there are illustrated as trihydric alcohols such as glycerol, trimethylol-ethane, trimethylolpropane and the like; and polyester-polyols and polyether-polyols and the like.

Polyoling and isocyanurating reactions are also carried out in the presence or absence of solvents which are inert to isocyanate radicals and dissolve the produced polycyclic compound well; for example, acetates such as ethylacetate, butylacetate, Cellosolve acetate (hereinafter referred to as celloacetate), aromatic hydrocarbon such as toluene, xylene and the like; furthermore, all kinds of solvents usable for polyoling reaction and urethanization reaction, may be equally used for both reactions.

For the isocyanuration of the invention, potassium or sodium salt of the carboxylic acid mentioned above is used as a catalyst. Examples of the carboxylic acid of the catalysts usable in the invention are propionic acid, butylic acid, valeric acid, caproic acid, heptanoic acid, caprylic acid, pelargonic acid, capric acid, undecyl icacid and the potassium, or sodium salt of branched compounds of these carboxylic acids.

In conventional isocyanuration reactions, isocyanuration is carried out at a temperature of about 60° to 100° C. for 20 to 100 hours in the presence of a conventional catalyst in an amount less than 0.25%, preferably 0.001 to 0.25%, by weight as based on the amount of HDI.

In the present invention using novel catalysts and partially polyoled HDI, the reaction is smoothly carried out in the absence or presence of solvent at a temperature lower than 100° C., more preferably about 35° to 70° C., and its reaction time is greatly shortened to about 4 to about 7 hours as compared with a conventional method. Formation of insoluble materials is also controlled in such a small amount that turbidity is not produced in the product of the present invention.

In the invention, the catalyst is used in an amount less than 0.25%, preferably 0.01 to 0.25%, by weight of HDI.

The amount of a catalyst may be decreased by using a promoter. In this case, the catalyst may be used in an amount of 0.001 to 0.1% by weight, and the promoter is used in an amount of 0.01 to 0.2% by weight as based on the weight of HDI. In case of using a promoter in an amount less than 0.01% by weight, the reaction time becomes longer, and in case of more than 0.2% by weight, unnecessary reaction will cause to form a highly viscous product of gelation.

Promoters may be phenolic hydroxyl compounds or alcoholic hydroxyl compounds or tertiary amines. By using a promoter, the reaction advances more smoothly.

Phenolic hydroxyl compounds may be illustrated as phenol, cresol, and trimethylphenol. Alcoholic hydroxyl compounds may be mentioned as ethanol, cyclohexanol and ethyleneglycol, etc. Tertiary amines may be triethylamine, methylpyridine, benzyldimethylamine, etc.

Progress of the isocyanuration reaction of the invention can be traced by titrating the amount of isocyanate radicals existing in the reaction system according to the titration method of ASTM D 1683. When the desired level of decrease of isocyanate radicals is reached, the reaction is stopped by adding a reaction stopper to the reaction mixture. Accordingly, the NCO content and viscosity of the reaction product can freely be controlled in accordance with the NCO content of the reaction mixture. The isocyanuration reaction is desirably stopped at a reaction rate of 20 to 60 mol% based on the theoretical rate of the reaction. As a reaction stopper, strong acid, for example, phosphoric acid, sulfuric acid or the like, may be used in the invention. The reaction stopper is used in 0.5 to 5.0 equivalent amount of the catalyst used.

The obtained reaction product is treated by conventional methods such as extraction, distillation or the like. In the case of a solvent, after recovering it, the unreacted HDI is recovered as much as possible. In view of the toxicity of HDI, the HDI content in the product of the invention is preferably less than 3.0% by weight. When the product is in the form of a solution of an organic solvent, the same HDI content is also used. Content of the final product can be measured by gas chromatography.

Because a characteristic peak of the trimer clearly appears in the neighborhood of a molecular weight of 504 by means of liquid chromatography, the amount of trimer can be easily quantitatively measured from the peak. Formation of the dimer is confirmed by absorption appearing at 1780 cm$^{-1}$ infrared spectrum.

The isocyanurated compound of the invention can be advantageously used as a raw material for urethane paint compositions which yields excellent properties such as high heat and light resistance, superior non-yellowing property, low toxicity, etc. These compounds are used in combination with polyols having a molecular weight higher than 600. However, in this case the trimer content in the whole isocyanurated products is preferably more than 10% by weight. If it is less than 10% by weight, there is a tendency to decrease heat and light resistance of the products.

As polyols having a molecular weight higher than 600, all types of the polyols having plural hydroxyl radicals in a molecule may be used. Typical examples of these polyols are polyesterpolyol, polyetherpolyol, acrylpolyol, epoxypolyol and the like.

The polyester-polyols can be prepared by a known method of reacting one or more compounds having at least two hydroxyl radicals with one or more compounds having at least two carboxylic radicals.

Examples of polyols for polyesterpolyols are ethylene-glycol, diethylene-glycol, triethylene-glycol, 1,2-propylene-glycol, trimethylene-glycol, 1,3-butylene-glycol, tetramethylene-glycol, hexa-methylene-glycol, deca-methylene-glycol, glycerol, trimethylol propane, pentaerythritol, sorbitol and the like.

Examples of carboxylic acids for polyesterpolyols are malonic acid, maleic acid, succinic acid, adipic acid, tartaric acid, pimelic acid, sebacic acid, oxalic acid, phthalic acid, terephthalic acid, azelaic acid, trimellitic acid and the like.

Lactone-polyester obtained by rings opening polymerization of a monomer having a lactone ring such as ε-caprolactam ε-valerolacton and the like are included in these polyesterpolyols. These polyols may be used in combination with two or more kinds of polyols.

Polyetherpolyols are prepared by addition-polymerizing, according to a known method using an initiator, at least one monomer selected from ethyleneoxide, propyleneoxide, butyleneoxide, styreneoxide, epichlorohydrin and the like, with at least one kind of the compounds having at least two active hydrogen stoms such as ethylene-glycol, diethylene-glycol, triethylene-glycol, 1.2-propylene-glycol, trimethylene-glycol, 1.3-butylene-glycol, tetramethylene-glycol, hexamethylene-glycol, glycerol, sorbitol, saccharose, trimellitic acid, bisphenol A, ethylenediamine, propylenediamine, diethylenetriamine or the like.

As acrylpolyols, a copolymerized polymer of hydroxyalkyacrylate with combination of alkylacrylate and a monomer copolymerization therewith is used.

As hydroxyalkyl acrylates, 2-hydroxyethyl-acrylate, 2-hydroxybutyl-acrylate, 2-hydroxyethyl-methacrylate, 2-hydroxypropyle-methacrylate, hydroxypropylacrylate, hydroxybutylmethacrylate and the like can be mentioned. As alkylacrylates, there can be mentioned those having carbon numbers of 2 to 16, for example, ethylacrylate, butylacrylate, 2-ethylhexylacrylate, methylmethacrylate, ethylmethacrylate, butylmethacrylate, 2-ethylmethacrylate, laurylmethacrylate and the like.

As a co-polymerizable compound, styrene, dibutylfumarate, dibutylmaleate, allylalcohol and the like can be mentioned.

If a polyol compound having a molecular weight higher than 600 is used, the obtained paint film becomes too hard and brittle to be used to paint.

The main components of the paint composition of the invention are prepared in a form of a mixture of derivative or polymers of HDI with polyol in the NCO/OH ratio of 0.8 to 1.2.

Solvents generally used to paint are such as toluene, xylene, ethyl acetate, butylacetate, celloacetate, methylethylketone and the like. They are also preferably used in the invention.

In making up a paint composition according to the invention, other necessary components usually used in the art, for example, pigment, plasticizer, leveling agent, surfactant, other fillers and additives are also added.

As is usual in paint making, these materials are mixed, and the mixture is passed through the steps of milling, dispersion, etc. to obtain a paint composition. The formulation of the obtained polyurethane paint can be of any type. However, two-package type paint is the most popular.

The paint composition of the invention is quite suitable for all-weather resistant paint without adding any additive such as oxidation resistant agent or ultra-violet absorbing agent, because isocyanurate rings themselves possess superior heat and weather resistance properties; low toxicity is also a feature of the paint composition of the invention.

The paint composition formulated above can be applied to a substrate by any known application method of painting such as spraying, brushing, dipping, flow coating, roll coating, knife coating or the like. Hardening is conducted at an ordinary temperature or under heating, although hardening conditions differ with a substrate applied to and, if necessary, can be accelerated by adding a hardening catalyst thereto.

The invention is explained in detail by way of examples in the following only for illustration; the invention should be construed only on the basis of the appended claims without any restriction thereof. It is apparent that numerous alterations, omissions and additions may be made without departing from the spirit thereof.

In the following, the products obtained were tested on their compatibility with Desmophen 800 (Polyester polyol produced by Nippon Urethane Corporation) and Epicoat 1001 (Epoxypolyol produced by Shell Corporation).

The test method and results obtained are shown as follows:

Compatibility Test (1) Test Method:

A mixed solvent of ethylacetate, butylacetate, toluene and celloacetate in the weight ratio of 1:1:1:1 was prepared, and a polyol was dissolved therein at a solid content of 40%. The test isocyanurated compound and polyol liquor obtained below were mixed in a beaker in the NCO:OH ratio of 1:1.

(2) Determination:

With the naked eye, specimens generating turbidity and/or insoluble materials were disqualified.

(3) Results:

The obtained solution of the products in Examples 1 to 11 and Comparative Examples 1 to 5 were clear and showed good results.

In Examples 1 and 12 and Comparative Examples 4 and 5, paint film tests were carried out. The tests method are as follows:

Film Test (1) Preparation of paint composition:

Predetermined amounts of polyols, pigments, solvent and the like are mixed in a paint conditioner in the ratios shown in Table 3 to prepare polyol component liquors. An isocyanurate component and a polyol component are mixed in the ratio shown in Table 2; the mixture is diluted with a diluting solvent in the ratio shown in Table 2. The obtained paint compositions are applied to a mild steel plate (Bondelight No. 1077) with a spray in a thickness of 30μ and leave them as they are for 7 days at a temperature of 25° C.; then after peeling out the films from the steel plate, they are tested according to the following test method. The results are shown in Table 3.

(2) Test method:

(a) A weather resistance test is carried on for a period of 400 to 1600 hours under the conditions of a temperature of 63° C.±3° C. and rainflowing of 9 minutes/hour.

From each specimen, degree of yellowing (ΔY) and gloss holding ratio (%) are calculated respectively according to Film Test Method No. 2 of the Japanese Paint Examination Association and JIS Z-8741. The results are shown in Table 3.

(b) With respect to heat yellowing resistance, tests are made under the conditions of 200° C. and 250° C. for 30 to 120 minutes using a hot air drier, and ΔY are calculated from each specimen according to Film Evaluating Standard of the Japanese Paint Examination Association.

(c) With regard to warm water resistance, specimens are dipped in warm water of 50° C. for a period of 1 to 6 weeks and evaluated according to Film Evaluating Standard of the Japanese Paint Examination Association. The results are shown in Table 3.

EXAMPLE 1 (Product used for film tests)

In a 500 ml four-necked flask provided with a thermometer, an agitator and a nitrogen seal tube, 100 parts of HDI and 0.8 part of 1.3 BG were charged. Air in the flask was replaced with nitrogen. After the flask was warmed at a temperature of 30° C., reaction continued for 2 hours. The NCO content was determined to be 48.8%. The reaction mixture obtained was a transparent colorless liquor.

Then 0.02 part of potassium caprate as a catalyst and 0.1 part of phenol as a promoter were added to the flask; after isocyanurating reaction continued for 4.5 hours, a transparent pale yellow liquid having an NCO content of 42% was obtained.

As a reaction stopper, 0.014 part of phosphoric acid was added to the mixture. After this reaction mixture was agitated for one hour, unreacted free HDI was removed using a molecular distillation apparatus.

The product obtained was transparent and pale yellow. The NCO content thereof was 21.0%; viscosity, 2300 cps/25° C.; free HDI, 0.7%.

In infrared spectrum, characteristic absorption of the isocyanurated compound at 1,680 cm$^{-1}$ was observed.

The products of this example were used as controls in the comparative test of Example 1 and Comparative Examples 4 and 5.

EXAMPLES 2, 6 and 9 (Polyolization reaction at 70° C. for 2 hours)

Using 3.4 parts of 1.3 BG in Examples 2 and 9, and 9.3 parts of pp-100 in Example 6 instead of 0.8 part of 1.3 BG in Example 1, the procedure was repeated at a reaction temperature of 70° C. to obtain polyoled products having NCO contents 45.3%, 44.9% and 45.3% respectively.

To the obtained products, 0.02 part of potassium propionate as a catalyst and 0.1 part of phenol as a promoter; 0.25 part of sodium propionate as a catalyst and no promoter; and 0.03 part of potassium undecylate as a catalyst and 0.1 part of phenol as a promoter were added respectively, and each reaction was conducted respectively at 55° C. for 5 hours; at 60° C. for 6 hours; at 55° C. for 5 hours, to obtain products having NCO contents 45.3%, 44.9% and 45.3% respectively.

As a reaction stopper, 0.026, 0.383 and 0.020 part of phosphoric acid was added to the reaction mixtures respectively and agitated to stop the reaction. All the obtained reaction liquors were transparent, pale yellow liquids.

The reaction liquors were subjected to molecular distillation to remove unreacted HDI and obtain transparent liquid having a pale yellow color. The NCO contents, viscosities and HDI contents were as follows:

| Example No. | 2 | 6 | 9 |
| --- | --- | --- | --- |
| NCO content (%) | 19.2 | 13.0 | 17.8 |
| Viscosity (cps/25° C.) | 2,900 | 28,000 | 44,000 |
| HDI content (%) | 0.5 | 0.4 | 0.6 | in infrared spectra of each product, strong absorption at 1,680 cm$^{-1}$ was observed, and one at 1,780 cm$^{-1}$ of dimer was not observed.

EXAMPLES 3, 4, 5 and 10 (Polyolization reaction at 80° C. for 2 hours)

Reaction in these examples was carried out at a temperature of 80° C. for 2 hours following the procedure of Example 1 using 100 parts of HDI in each Eeample and 1.1, 4.4, 5.0 parts of 1.6 HG in Examples 3, 4 and 10 respectively, and 9.3 parts of pp-100 in Example 5 instead of 0.8 part of 1.3 BG in Example 1; transparent, colorless polyoled reaction liquorshaving NCO contents of 48.6%, 44.9%, 44.9% and 45.2% were obtained in the Examples 3,4,5 and 10.

In Example 3, 0.1 part of potassium undecylate was added to the reaction liquor without a promoter; in Examples 4, 5 and 10, 0.1 part of phenol, a promoter, and 0.01 part of sodium undecylate; 0.02 part of sodium caprate; 0.03 part of sodium propionate were used respectively. Their reactions were continued for 5 hours at 60° C. in Examples 3 and 4, and at 50° C. in Examples 5 and 10. Each obtained reaction liquor included 41.5%, 34.8%, 38.0% and 38.8% of NCO content. Then 0.066 part, 0.014 part, 0.015 part and 0.067 part of phosphoric acid were added to the respective obtained liquors; the reactions were stopped to obtain transparent, pale yellow liquors. These reaction liquors were subjected to molecular distillation to recover unreacted HDI and obtained transparent products having a pale yellow color. The NCO contents, viscosities and HDI contents were as follows:

| Example No. | 3 | 4 | 5 | 10 |
|---|---|---|---|---|
| NCO content (%) | 20.6 | 18.1 | 16.2 | 19.4 |
| Viscosity (cps/25° C.) | 3,100 | 2,900 | 1,800 | 3,100 |
| HDI content (%) | 0.8 | 0.9 | 0.9 | 0.6 |

In all the products, strong absorption at 1,680 cm$^{-1}$ was observed in infrared spectrum, but one at 1,780 cm$^{-1}$ did not appear.

EXAMPLES 7 and 8 (Solvent used for polyolization)

In Examples 7 and 8, 0.8 part of 1.3 BG and 4.4 parts of 1.6 HG were used as a polyol and 50 parts of celloacetate as a solvent in both Examples; their polyolization reactions were continued at 80° C. for 2 hours. Products having NCO contents of 32.5% and 29.9% were obtained.

To these respective products, a catalyst, 0.02 part of potassium propionate, with a promoter, 0.1 part of phenol; and a catalyst, 0.02 part of potassium caprate without a promoter, were added. Each reaction was kept at a temperature of 60° C. for 6 and 5.5 hours.

Each product was a pale yellow, transparent liquor having NCO content of 28.0% and 22.2%; 0.026 and 0.140 part of phosphoric acids were added to them to stop the reactions. The reaction mixture agitated were subjected to distillation to remove solvents and unreacted HDI.

The NCO contents, viscosities and HDI contents of the products were as follows:

| Example No. | 7 | 8 |
|---|---|---|
| NCO content (%) | 21.5 | 18.4 |
| Viscosity (cps/25° C.) | 2,100 | 4,000 |
| HDI content (%) | 0.8 | 0.6 |

EXAMPLE 11

7.2 parts of 1.3 BG was added to 100 parts of HDI. Polyolization reaction was conducted at 80° C. for 2 hours under N$_2$ atmosphere to obtain a colorless transparent reaction liquor having an NCO content of 39.8%.

0.02 part of sodium caprate, a catalyst, and 0.1 part of phenol, a promoter, were added to the reaction product; then the reaction was conducted at 60° C. for 5 hours to obtain a reaction liquor having a NCO content of 31.5%. 0.015 part of phosphoric acid was added to the reaction mixture, which was agitated to stop the reaction to obtain a product having a transparent pale yellow color by removing unreacted HDI by molecular distillation. The NCO content, viscosity and HDI content were 16.0%, 200,000 cps/25° C. and 0.5% respectively.

In infrared spectrum of the product showed strong absorption at 1,680 cm$^{-1}$ but did not show at 1,780 cm$^{-1}$. The specimen of the compatibility test was clear and good.

COMPARATIVE EXAMPLE 1 (Excessive catalyst was used)

Example 1 was repeated using the catalyst (0.4 part of potassium caprate) and promoter (0.5 part of phenol).

Though start temperature of the reaction was 60° C., it rose higher and higher as the reaction advanced; the content of a flask started becoming light-brown and highly viscous. Then it became impossible to keep the reaction temperature at 60° C.

Infrared analysis showed that 75 mol% of the isocyanate radicals was consumed.

COMPARATIVE EXAMPLE 2 (Too high reaction temperature was used)

Example 2 was repeated and the same polyoled product as in Example 2 having NCO content of 45.3% was obtained.

Isocyanurating reaction was carried out at a temperature of 120° C. using the same catalyst and promoter in the same amount of Example 2; the content of a flask became brown color, and the viscosity and temperature rose rapidly to produce a gel and the reaction cannot be continued.

As a result of the infrared analysis, 70 mol% of isocyanate radicals was found consumed.

COMPARATIVE EXAMPLE 3 (Poly-functional polyol was used)

100 parts of HDI was mixed with 5 parts of "Quodrol" (a polyol manufactured and sold by Denka Kogyo Co., prepared by addition reaction of ethylene diamine and propylene oxide and has functionality of 4 and a hydroxyl value of 760). After 2-hour polyoling reaction at 70° C., a clear, colorless mixture having an NCO content of 44.1% was obtained. To the reaction mixture, 0.02 part of potassium propionate as a catalyst and 0.1 part of phenol as a promoter were added. After 5-hour isocynurating reaction at 55° C., the liquor became pale yellow and gelated.

In the following Comparative Examples, compatibility test and film test were carried out. The obtained results are shown in Tables 1 and 2 to 3.

COMPARATIVE EXAMPLE 4 (Polyol having too high molecular weight was used to polyolization)

50 parts of polyetherpolyol T-4000 (manufactured and sold by Asahi Denka Co., Ltd.: molecular weight 4000, functionality 3, hydroxyl value 42) was used as a polyol. Under the same reaction conditions as in Example 1, 100 parts of HDI was polyoled with the polyol mentioned in the above to obtain a polyoled transparent and colorless liquor of 30.5% NCO content. Isocyanuration was carried out using 0.10 part of potassium undecylate as a catalyst and 0.1% of phenol as a promoter. A transparent, pale yellow reaction liquor of 26.5% NCO content was obtained; the liquor was distilled, and unreacted HDI was recovered as in Example 5 to obtain a pale yellow, transparent product having NCO content of 5.5%, viscosity of 8,200 cps/25° C. and HDI content of 0.6%.

The product was not abnormal in infrared spectrum or in the compatibility test, but in the paint test, results of all test items were unsatisfactory.

COMPARATIVE EXAMPLE 5 (Too much polyol was used)

According to Example 1, polyolization was carried out using 100 parts of HDI and 14 parts of 1.6 HG to obtain a polyolization product of 34.1% NCO content; to the product, 0.02 part of sodium caprate and 0.1 part of phenol were added for isocyanuration, obtaining a pale yellow, transparent liquor of 30.0% NCO content.

0.015 part of phosphoric acid was added to the product obtained above to stop reaction. Unreacted HDI was removed by molecular distillation; the obtained product was transparent and had 15.0% NCO content, 100,000 cps/25° C. viscosity, and 1.5% HDI content.

Results of the tests of the reaction mixture for infrared spectrum and compatibility were good as in Example 1 and Comparative Example 4 though the ones of the paint test were not good as shown in Table 3.

EXAMPLE 12 (Paint film test)

Only paint film test was conducted, and no compatibility test of the product was carried on.

0.8 part of 1.3 BG was added to 100 parts of HDI; after 2-hour urethanization reaction at a temperature of 80° C. according to Example 1, a transparent liquor of 48.7% NCO content was obtained. Adding 0.1 part of sodium caprate and 0.1 part of phenol to it, reaction was taken place at 40° C. for 6 hours according to Example 1. The reaction mixture was a clear transparent liquid of 41.9% NCO content. 0.05 part of phosphoric acid was added to the mixture to stop the reaction. By molecular distillation, unreacted HDI was recovered. The product was transparent, yellow and had NCO content of 21.0%, viscosity of 2,350 cps/25° C. and trimer content of 52.0%. Dividing the product into two parts, Desmophene 800 (No. 1) and A-801 (No. 2: acrylpolyol prepared by Dinihon Ink Co.) were added to each part respectively, and pigment, a solvent and a dilution solvent were added to them: the obtained two kinds of paint compositions (Nos. 1 and 2, see Table 4) were subjected to the paint film tests. The results are shown in Table 5.

As shown in Tables 4 and 5, the product of this example gave good test results in the paint film test.

TABLE 1

| | Example No. | | | | | | | | | | | | Comparative Example No. | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 1 | 2 | 3 | 4 | 5 |
| Raw Materials | | | | | | | | | | | | | | | | | |
| HDI (part)* | 100 | 100 | 100 | 100 | 100 | 100 | 100 | 100 | 100 | 100 | 100 | 100 | 100 | 100 | 100 | 100 | 100 |
| Solvent (part) | | | | | | | | | | | | | | | | | |
| Celloacetate | | | | | | | 100 | 100 | | | | | | | | | |
| Polyol (part) | | | | | | | 50 | 50 | | | | | | | | | |
| 1.3 BG | 0.8 | 3.4 | | | | | | | | | | | 0.8 | 3.4 | | | |
| 1.6 HG | | | 1.1 | 4.4 | 8.3 | 8.3 | 0.8 | 4.4 | 3.4 | 5.0 | 7.2 | 0.8 | | | | | |
| PP-1000 | | | | | | | | | | | | | 5.0** | 5.0*** | | | 14.0 |
| Polyolization | | | | | | | | | | | | | | | | | |
| Polyolization Reaction | | | | | | | | | | | | | | | | | |
| Temperature (°C) | 80 | 70 | 80 | 80 | 80 | 70 | 80 | 80 | 70 | 80 | 80 | 80 | 80 | 70 | 70 | 80 | 80 |
| Hour (h) | 2 | 2 | 2 | 2 | 2 | 2 | 2 | 2 | 2 | 2 | 2 | 2 | 2 | 2 | 2 | 2 | 2 |
| Reaction Mixture | | | | | | | | | | | | | | | | | |
| Appearance | Colorless, transparent liquor | | | | | | | | | | | | | Colorless, transparent liquor | | Colorless, transparent liquor | |
| NCO content (%) | 48.8 | 45.3 | 48.6 | 44.9 | 44.9 | 44.9 | 32.5 | 29.9 | 45.3 | 45.2 | 39.8 | 48.7 | 48.8 | 45.3 | 44.1 | 30.5 | 34.1 |
| Isocyanuration | | | | | | | | | | | | | | | | | |
| Catalyst for Isocyanuration (part) | | | | | | | | | | | | | | | | | |
| Potassium capriate | 0.02 | | | | | | | | | | | | | | | | |
| Potassium propionate | | 0.02 | | | | | | | | | | | | | | | |
| Potassium undecylate | | | 0.10 | | | | | | | | | 0.03 | | | | | |
| Sodium caprate | | | | | 0.02 | | 0.02 | 0.02 | | | 0.02 | | 0.4 | 0.02 | 0.02 | | 0.02 |
| Sodium propionate | | | | 0.01 | | 0.25 | | | | | | | | | | | |
| Sodium undecylate | | | | | | | | | | | | | | | | | |
| Poatassium acetate | | | | | | | | | 0.08 | | | | | | | | |
| Potassium stearate | | | | | | | | | | 0.08 | | | | | | | |
| Lithium stearate | | | | | | | | | | | | 0.1 | | | | | |
| Tributylphosphine | | | | | | | | | | | | | | | | | |
| Promoter (part) | | | | | | | | | | | | | | | | | |
| Phenol | 0.1 | 0.1 | | 0.1 | 0.1 | | 0.1 | | 0.1 | 0.1 | 0.1 | 0.1 | 0.5 | 0.1 | 0.1 | 0.1 | 0.1 |
| Isocyanurating Reaction | | | | | | | | | | | | | | | | | |
| Temperature (°C) | 60 | 55 | 60 | 60 | 50 | 60 | 60 | 60 | 50 | 50 | 60 | 40 | 60 | 120 | 55 | 60 | 60 |
| Hour (h) | 4.5 | 5 | 5 | 5 | 5 | 6 | 6 | 5.5 | 5 | 5 | 5 | 6 | | | 5 | 5 | 5 |
| Stopping Agent (part) | 0.014 | 0.026 | 0.066 | 0.014 | 0.015 | 0.383 | 0.026 | 0.140 | 0.020 | 0.087 | 0.015 | 0.050 | | | | 0.066 | 0.015 |
| Phosphoric acid | | | | | | | | | | | | | | | | | |
| Reaction Mixture | | | | | | | | | | | | | | | | | |
| Appearance | Pale yellow, transparent | | | | | Pale yellow, transparent | | | Pale yellow, transparent | | | | Pale brown, gelated | Brown gelated | Pale yellow, gelated | Pale yellow, transparent | Pale yellow, transparent |
| NCO content (%) | 42.0 | 38.4 | 41.5 | 34.8 | 38.0 | 29.2 | 28.0 | 22.2 | 31.4 | 38.8 | 31.5 | 41.9 | | | | 26.5 | 30.0 |
| Products | | | | | | | | | | | | | | | | | |
| After Distillation | | | | | | | | | | | | | | | | | |
| Appearance | | | | | | | | | | | | | | | | Pale yellow, transparent | Pale yellow, transparent |
| NCO content (%) | 21.0 | 19.2 | 20.8 | 18.1 | 16.2 | 18.0 | 21.5 | 18.4 | 17.8 | 19.4 | 18.0 | 21.0 | | | | 5.5 | 15.0 |
| Viscosity (cps/25° C.) | 2,300 | 2,900 | 3,100 | 4,200 | 1,800 | 28,000 | 2,100 | 4,000 | 44,000 | 3,100 | 20,000 | 2,350 | | | | 8,200 | 100,000 |
| Free HDI (%) | 0.7 | 0.5 | 0.8 | 0.9 | 0.9 | 0.4 | 0.8 | 0.8 | 0.8 | 0.8 | 0.5 | 0.5 | | | | 0.6 | 0.5 |
| Inspection of Infrared | Occurence of isocyanuration was recognized. (Trimer 52.0%) | | | | | | | | | | | | | | | | |

TABLE 1-continued

| | Example No. | | | | | | | | | | | | Comparative Example No. | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 1 | 2 | 3 | 4 | 5 |
| Spectrum | | | | | | | | | | | | | | | | | |
| Compatibility | | | | | | Transparent | Transparent | | | | | | | | | Transparent | |
| Desmophene 800 | | | | | | | | | | | | | | | | Transparent | |
| Epicoat 1001 | | | | | | | | | | | | | | | | | |

*part by weight
**Quadol: Polyether having four functionalities and a hydroxyl value of 4 prepared by Asahi Denka Kogyo Co., Ltd. (by additive reaction of propyleneoxide to ethylene-diamine)
***T-4000: Polyether having a molecular weight of 4,000, three functionalities and a hydroxylic value of 760 prepared by Asahi Denka Kogyo Co., Ltd.

TABLE 2

|  |  | Example No. 1 | Comparative Example No. 4 | Comparative Example No. 5 |
|---|---|---|---|---|
| Isocyanurate Compound (part) |  | 100 | 100 | 100 |
| Polyol Component |  |  |  |  |
| Polyol | Desmophene 800 (part) | 96 | 25.4 | 69.1 |
| Pigment | Taicoupe R-930 (part) Note 3. | 131 | 84 | 113 |
| Solvent | D/D solvent (part) Note 4. | 157 | 100 | 135 |
| Diluting Solvent | (part) Note 4. | 450 | 450 | 450 |

Note 3. Prepared by Ishihara Sangyo Co., Ltd.; Titanium Oxide
Note 4. Ethyl Acetate:Toluene:Butyl Acetate:Celloacetate = 1:1:1:1

TABLE 3

|  |  |  | Example No. 1 | Comparative Example No. 4 | Comparative Example No. 5 |
|---|---|---|---|---|---|
| Weather Resistance Note 5. | Degree of Yellowing (ΔYI) Note 8. | 400 (hr) | 0.9 | 1.2 | 1.2 |
|  |  | 800 | 1.3 | 2.6 | 2.7 |
|  |  | 1200 | 1.5 | 3.3 | 3.5 |
|  |  | 1600 | 1.8 | 3.9 | 4.1 |
|  | Gloss Holding Ratio (%) Note 9. | 400 (h) | 98 | 88 | 86 |
|  |  | 800 | 91 | 63 | 60 |
|  |  | 1200 | 82 | 45 | 43 |
|  |  | 1600 | 79 | 25 | 24 |
| Heat Yellowing Resistance Note 6. | 200° C. (ΔYI) Note 7. | 30 (min.) | 3.0 | 12.0 | 31.0 |
|  |  | 60 | 9.2 | 32.0 | 48.0 |
|  |  | 120 | 15.8 | 55.0 | 60.0 |
|  | 250° C. (ΔYI) Note 7. | 30 (min.) | 3.0 | 58.2 | 62.5 |
|  |  | 60 | 9.1 | 72.0 | 83.0 |
|  |  | 120 | 15.7 | 88.1 | 96.0 |
| Warm Water Resistance Note 7. | Dipping at 50° C. | 1 (week) | normal | normal | normal |
|  |  | 2 | normal | 8S | 8VS |
|  |  | 4 | normal | 6M | 8L |
|  |  | 6 | normal | 4M | 6M |

Note 5. Sunshine Type Weathermeter, Temperature 63 ± 3° C. Rain Flowing 9 min./60 min.
Note 6. By hot air drier.
Note 7. According to Paint Film Evaluating Standard of Japanese Paint Examination Association.
Note 8. According to Paint Testing Method No. 2 of Japanese Paint Examination Association.
Note 9. According to JIS Z - 8741

TABLE 4

|  |  | Example 12 (No. 1) |
|---|---|---|
| HDI polymers or derivatives each 100 parts |  | Isocyanurate obtained in Example 12 |
| Polyol Component |  |  |
| Polyol | Desmophene 800 (part) Note 10. | 96 |
| Pigment | Taicoupe R-930 (part) Note 11. | 131 |
| Solvent | D/D solvent (part) Note 12. | 157 |
| Diluting Solvent | (part) Note 12. | 450 |

|  |  | Example 12 (No. 2) |
|---|---|---|
| HDI polymers or derivatives each 30 parts |  | Isocyanurate obtained in Example 12 |
| Polyol Component |  |  |
| Polyol | A-801 (part) Note 13. | 168 |
| Pigment | Taicoupe R-930 (part) | 76 |
| Solvent | Xylene (part) | 90 |
| Diluting Solvent | (part) Note 14. | 270 |

Note 10. Prepared by Nippon Polyurethane Industry Co., Ltd.; Polyester (M.W. 800)
Note 11. Prepared by Ishihara Sangyo Co., Ltd.; Titanium Oxide
Note 12. Ethyl Acetate:Toluene:Butyl Acetate:Celloacetate = 1:1:1:1
Note 13. Acrylpolyol (M.W. 11,600) prepared by Dainihon Ink Co., Ltd.
Note 14. Ethyl Acetate:Butyl Acetate:Celloacetate = 1:1:1

TABLE 5

|  |  |  | Example 12 No. 1 | Example 12 No. 2 |
|---|---|---|---|---|
| Weather Resistance | Degree of Yellowing (ΔYI) | 400 (h) | 0.9 | 0.8 |
|  |  | 800 | 1.2 | 1.0 |
|  |  | 1200 | 1.5 | 1.1 |
|  |  | 1600 | 1.8 | 1.1 |
|  | Gloss Holding Ratio (%) | 400 (h) | 98 | 99 |
|  |  | 800 | 91 | 98 |
|  |  | 1200 | 83 | 92 |
|  |  | 1600 | 79 | 91 |
| Heat Yellowing Resistance | 200° C. (ΔYI) | 30 (min.) | 3.0 | 0.8 |
|  |  | 60 | 9.3 | 3.5 |
|  |  | 120 | 15.8 | 7.9 |
|  | 250° C. (ΔYI) | 30 (min.) | 3.0 | 9.8 |
|  |  | 60 | 9.3 | 12.9 |
|  |  | 120 | 15.8 | 14.8 |
| Warm Water Resistance | Dipping at 50° C. | 1 (week) | normal | normal |
|  |  | 2 | normal | normal |
|  |  | 4 | normal | normal |
|  |  | 6 | normal | normal |

What is claimed is:

1. A process for preparing an isocyanurated compound of hexamethylene diisocyanate which comprises the following steps:
   (a) partially polyoling hexamethylene diisocyanate using a polyol compound in an amount less than 15 mol %, and then recovering unreacted hexamethylene diisocyanate from the reaction mixture,
   (b) trimerising said polyoled hexamethylene diisocyanate in the presence of a catalyst having the formula (1), $$C_nH_{2n+1}COOM \qquad (1)$$

wherein n stands for an integer of 2 to 10, $C_nH_{2n+1}$ for a straight or branched alkyl radical and M for a potassium or sodium metal, and
   (c) stopping the trimerization reaction at a reaction ratio of less than 80%.

2. A process according to claim 1, wherein hexamethylene diisocyanate is polyoled in an amount less than 15 mol% of the isocyanate group in the reaction mixture.

3. A process according to claim 2, wherein a polyol used in polyolization is selected from the group consisting of polyols having a molecular weight less than 3,000 and having 2 to 3 functionalities.

4. A process according to 3, wherein said polyol is selected from the group consisting of polyester polyol polyhydric alcohol, dihydric alcohol and polyetherpolyol.

5. A process according to claim 1, wherein the polyolization is carried out at a temperature lower than 100° C., preferably at 70° to 90° C.

6. The process according claim 1, wherein n stands for integer of 3 to 9.

7. A process according to claim 1, wherein said catalyst is used in an amount of less than 0.25% by weight based on the amount of hexamethylene diisocyanate.

8. A process according to claim 7, wherein said catalyst is used in an amount of 0.01 to 0.25% by weight of hexamethylene diisocyanate.

9. A process according to claim 8, wherein a promoter is further co-used together the said catalyst.

10. A process according to claim 9, wherein said promoter is one selected from the group consisting of alcoholic compounds, phenolic hydroxylic compounds and tertiary amines.

11. A process according to claim 1, wherein the trimerization is carried out in the presence or absence of a solvent.

12. A process according to claim 11, wherein said solvent is selected from the group consisting of esters and aromatic hydrocarbons.

13. A process according to claim 1, wherein said trimerization is carried out at a temperature of 60° to 100° C.

14. A process according to claim 1, wherein said trimerization is carried out for about 4 to about 7 hours.

15. A process according to claim 1, wherein the trimerization reaction is stopped at 20 to 60 mol% based on the theoretical rate of reaction.

16. A process according to claim 15, wherein the reaction is stopped at a desired rate of reaction by adding a strong acid to the reaction mixture.

17. A process according to claim 16, wherein said strong acid is selected from phosphoric acid and sulfuric acid.

18. A paint composition which comprises an admixture of the product obtained by the process of claim 1, polyols in an amount of NCO/OH ratio 0.8 to 1.2, solvents and adjuvants.

19. A paint composition according to claim 18, wherein said isocyanurated compound of hexamethylene diisocyanate is used in an amount of more than 10% by weight based on the total amount of the composition.

20. A paint composition according to claim 18, wherein said polyol has a molecular weight of 600 to 3,000.

21. A paint composition according to claim 20, wherein said polyol is selected from the group consisting of polyester polyols, polyetherpolyols and acrylpolyols.

22. A paint composition of claim 18, wherein the solvent is selected from the group consisting of toluene, xylene, ethyl acetate, butyl acetate, celloacetate, and methylethylketone.

23. A paint composition of claim 18, wherein the adjuvant is selected from the group consisting of pigment, plasticizer, leveling agent, surfactant, and fillers.

* * * * *